(12) United States Patent
Brighton et al.

(10) Patent No.: US 7,130,692 B2
(45) Date of Patent: Oct. 31, 2006

(54) PORTABLE ELECTROTHERAPY DEVICE FOR TREATING OSTEOARTHRITIS AND OTHER DISEASES, DEFECTS AND INJURIES OF THE KNEE JOINT

(75) Inventors: Carl T. Brighton, Malvern, PA (US); Michael D. Carlozzi, Boston, MA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 203 days.

(21) Appl. No.: 10/603,226

(22) Filed: Jun. 25, 2003

(65) Prior Publication Data

US 2005/0010264 A1    Jan. 13, 2005

Related U.S. Application Data

(63) Continuation-in-part of application No. 10/457,167, filed on Jun. 9, 2003, now Pat. No. 7,022,506, which is a continuation-in-part of application No. 10/257,126, filed as application No. PCT/US01/05991 on Feb. 23, 2001.

(60) Provisional application No. 60/184,491, filed on Feb. 23, 2000.

(51) Int. Cl.
*A61N 1/18* (2006.01)

(52) U.S. Cl. .............. 607/50; 607/51; 607/69; 607/70; 607/76; 607/115; 607/149

(58) Field of Classification Search .......... 607/2, 607/68–72, 148–149, 144, 115, 3, 50–51, 607/76; 600/390–386
See application file for complete search history.

(56) References Cited

U.S. PATENT DOCUMENTS 4,266,533 A * 5/1981 Ryaby et al. ............ 600/14

(Continued)

FOREIGN PATENT DOCUMENTS

WO    WO 00/02585 A1    1/2000

(Continued)

OTHER PUBLICATIONS

Aaron, R.K., et al., "The conservative treatment of osteonecrosis of the femoral head," *Clin. Orthop.*, 1989, 249, 209-218.

(Continued)

*Primary Examiner*—Robert Pezzuto
*Assistant Examiner*—Shevon Johnson
(74) *Attorney, Agent, or Firm*—Woodcock Washburn LLP

(57) ABSTRACT

A portable device for applying therapeutic electrical signals and/or electromagnetic fields to a patient's knee for the treatment of osteoarthritis and other diseases, defects and injuries. The device is operable in several modes to deliver signals to the patients knee so as to cause an electric and/or electromagnetic field to be generated that selectively up-regulates gene expression of Aggrecan and Type II Collagen while simultaneously selectively down-regulating the gene expression of metalloproteases. The device includes a signal generator that generates compound electric signals including a 60 kHz sine wave having a peak to peak voltage of approximately 4.6 V to 7.6 V and a 100% duty cycle signal that is generated for approximately 30 minutes and a 50% duty cycle signal that is generated for approximately 1 hour after the 100% duty cycle signal. These compound electric signals are communicated to electrodes or coils in the proximity of a patient's knee for the generation of a specific and selective electromagnetic field that treats the diseased tissue.

14 Claims, 12 Drawing Sheets

U.S. PATENT DOCUMENTS

| | | | |
|---|---|---|---|
| 4,430,999 A | 2/1984 | Brighton et al. | 128/419 |
| 4,442,846 A | 4/1984 | Brighton et al. | 128/784 |
| 4,467,808 A | 8/1984 | Brighton et al. | 128/419 F |
| 4,487,834 A | 12/1984 | Brighton | 435/173 |
| 4,506,674 A | 3/1985 | Brighton et al. | 128/419 |
| 4,509,520 A | 4/1985 | Dugot | 128/419 |
| 4,535,775 A * | 8/1985 | Brighton et al. | 607/51 |
| 4,549,547 A | 10/1985 | Brighton et al. | 128/419 F |
| 4,600,010 A | 7/1986 | Dugot | 128/419 |
| 4,683,873 A | 8/1987 | Cadossi et al. | 128/1.5 |
| 5,014,699 A | 5/1991 | Pollack et al. | 128/419 |
| 5,038,797 A | 8/1991 | Batters | 128/798 |
| 5,269,746 A | 12/1993 | Jacobson | 600/13 |
| 5,273,033 A | 12/1993 | Hoffman | 607/46 |
| 5,338,286 A | 8/1994 | Abbott et al. | 600/14 |
| 5,374,283 A | 12/1994 | Flick | 607/46 |
| 5,565,005 A * | 10/1996 | Erickson et al. | 607/51 |
| 5,690,692 A * | 11/1997 | Fleming | 607/50 |
| 5,743,844 A | 4/1998 | Tepper et al. | 600/14 |
| 5,968,527 A | 10/1999 | Litovitz | 424/400 |
| 6,083,149 A | 7/2000 | Wascher et al. | 600/9 |
| 6,132,362 A | 10/2000 | Tepper et al. | 600/14 |
| 6,186,940 B1 | 2/2001 | Kirschbaum | 600/12 |
| 6,261,221 B1 | 7/2001 | Tepper et al. | 600/14 |
| 2002/0052634 A1 | 5/2002 | March | 607/50 |
| 2003/0211084 A1 | 11/2003 | Brighton et al. | 424/93.7 |

FOREIGN PATENT DOCUMENTS

| | | |
|---|---|---|
| WO | WO 01/62336 A1 | 8/2001 |
| WO | WO 2005/070136 A2 | 8/2005 |

OTHER PUBLICATIONS

Aaron, R.K., et al., "Stimulation of experimental endochondral ossification by low-energy pulsing electromagnetic fields," *J. Bone Miner. Res.*, Nov. 2, 1989, 4, 227-233.

Bassett, C.A.L., "Low energy pulsing electromagetic fields modify biomedical processes," *BioEssays*, 1987, 6(1), 36-42.

Bassett, C.A.L., et al., "Effects of pulsed electromagnetic fields on Steinberg ratings of femoral head osteonecrosis," *Clin. Orthop.*, Sep. 1989, 246, 172-185.

Bassett, C.A.L., "Fundamental and practical aspects of therapeutic uses of pulsed electromagnetic fields (PEMSs)," *Crit. Rev. Biomed. Eng.*, 1989, 17(5), 451-529.

Bassett, C.A.L., et al., "Pulsing electromagnetic field treatment in ununited fractures and failed arthrodeses," *JAMA*, Feb. 5, 1982, 247(5), 623-628..

Binder, A., et al., "Pulsed electromagnetic field therapy of persistent rotator cuff tendonitis," *Lancet*, Mar. 31, 1984, 695-698.

Brighton, C.T., et al., "A multicenter study of the treatment of non-union with constant direct current," *J. Bone and Joint Surgery*, Jan. 1981, 62-A(1), 2-13.

Brighton, C.T., et al., "Treatment of recalcitrant non-union with a capacitively coupled electrical field," *J. Bone and Joint Surgery*, Apr. 1985, 67-A(4), 577-585.

Brighton, C.T., et al., "Treatment of castration-induced osteoporosis by a capacitively coupled electrical signal in rat vertebrae," *J. Bone and Joint Surgery*, Feb. 1989, 71-A(2), 228-236.

Brighton, C.T., et al., "Increased cAMP production after short-term capacitively coupled stimulation in bovine growth plate chondrocytes," *J. Orthop. Res.*, 1988, 6, 552-558.

Brighton, C.T., et al., "Treatment of denervation/disuse osteoporosis in the rat with a capacitively coupled electrical signal: effects on bone formation and bone resorption," *J. Orthop. Res.*, 1988, 6, 676-684.

Goodman, R., et al., "Exposure of salivary gland cells to low-frequency electromagnetic fields alters polypeptide synthesis," *Proc. Natl. Acad. Sci. USA*, Jun. 1988, 85, 3928-3932.

Goodwin, C.B., et al., "A double-blind study of capacitively coupled electrical stimulation as an adjunct to lumbar spinal fusions," *Spine*, 1999, 24(13), 1349-1356.

Grodzinsky, A.J., "Electromechanical and physicochemical properties of connective tissue," *Crit. Rev. Biomed. Engng.*, 1983, 9(2), 133-198.

Harrison, M.H.M., et al., "Use of pulsed electromagnetic fields in perthes disease: report of a pilot study," *J. Pediatr. Orthop.*, 1984, 4, 579-584.

Jones, D.B., et al., "PEMF effects on differentiation and division in mirine melanoma cells are mediated indirectly through cAMP," *Trans. BRAGS 6*, 1986, 51.

Lorich, D.G., et al., "Biochemical pathway mediating the resopnse of bone cells to capacitive coupling," *Clin. Orthop. and Related Res.*, 1998, 350, 246-256.

Massardo, L., et al., "Osteoarthritis of the knee joint: an eight year prospective study," *Ann Rheum Dis.*, 1989, 48, 893-897.

Mooney, V., "A randomized double-blind prospective study of the efficacy of pulsed electromagnetic fields for inter body lumbar fusions," *Spine*, 1990, 15(7), 708-712.

Norton, L.A., et al., "Pulsed electromagnetic fields alter phenotypic expression in chondroblasts in tissue culture," *J. Orthop. Res.*, 1988, 6, 685-689.

Rodan, G.A., et al., "DNA synthesis in cartilage cells is stimulated by oscillating electric fields," *Science*, Feb. 10, 1978, 199, 690-692.

Ryaby, J.T., et al., "Pulsing electromagnetic fields affect the phosphorylation and expression of oncogene proteins," *Trans. BRAGS 6*, 1986, p. 78.

Ryaby, J.T., et al., "The effect of electromagnetic fields on protein phosphorylation and synthesis in murine melanoma cells," *BRAGS*, p. 32.

Wang, W., et al., "The increased level of PDGF-A constributes to the increased proliferation induced by mechanical stimulation in osteoblastic cells," *Biochem. And Molecular Biol. International.*, Oct. 1997, 43(2), 339-346.

Zhuang, H., et al., "Mechanical strain-induced proliferation of osteoblastic cells parallels increased TGF-β1 mRNA,"*Biochem. Biophys. Res. Commun.*, 1996, 229, 449-453.

Zhuang, H., et al., "Electrical stimulation induces the level of TGF-β1 mRNA in osteoblastic cells by a mechanism involving calcium/calmodulin pathway," *Biochem. Biophys. Res. Commun.*, 1997, 237, 225-229.

Brighton, C.T., et al., "Fracture healing in the rabbit fibula when subjected to various capacitively coupled electrical fields," *J. Orthop. Res.*, 1985, 3, 331-340.

Brighton, C.T., et al., "*In vitro* bone-cell response to a capacitively coupled electrical field," *Clin. Orthop. Related Res.*, Dec. 1992, 285, 255-262.

Carter, E.L., et al., "Field distributions in vertebral bodies of the rat during electrical stimulation: a parametric study," *IEEE Trans. on Biomed. Eng.*, Mar. 1989, 36(3), 333-345.

Chang, W.H., et al., "Enhancement of fracture healing by specific pulsed capacitively-coupled electric field stimulation," *Frontiers Med. Biol. Engng.*, 1991, 3(1), 57-64.

Brighton, C.T., et al., "Signal transduction in electrically stimulated bone cells," *J. Bone Joint Surg. Am.*, 2001, 83-A(10), 1514-1523.

Pienkowski, D., et al., "Low-power electromagnetic stimulation of osteotomized rabbit fibuiae," *J. of Bone & Joint Surgery*, 1994, 76-A(4), 489-501.

Wang, W., et al., "Up-regulation of chondrocyte matrix genes and products by electric fields," *Clin. Orthopaedics & Related Res.*, 2004, 427S, S163-S173.

\* cited by examiner

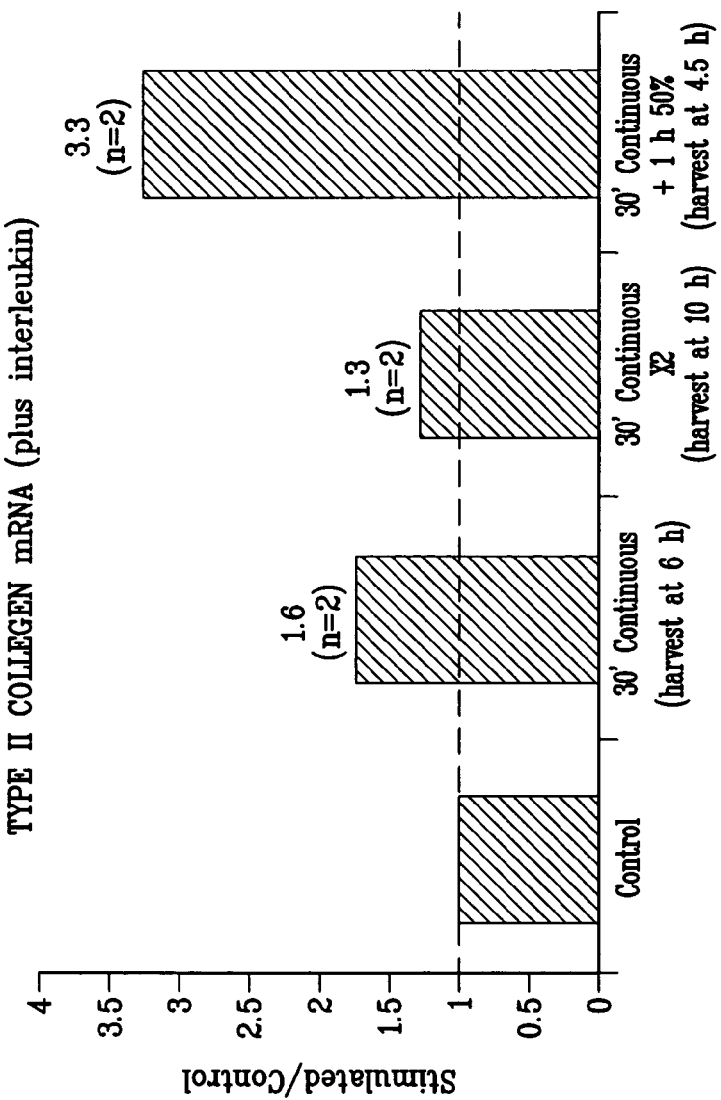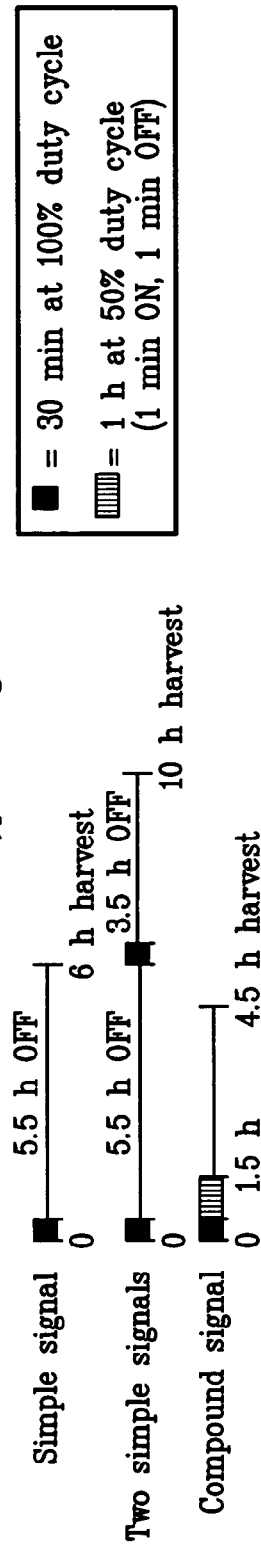
FIG. 3

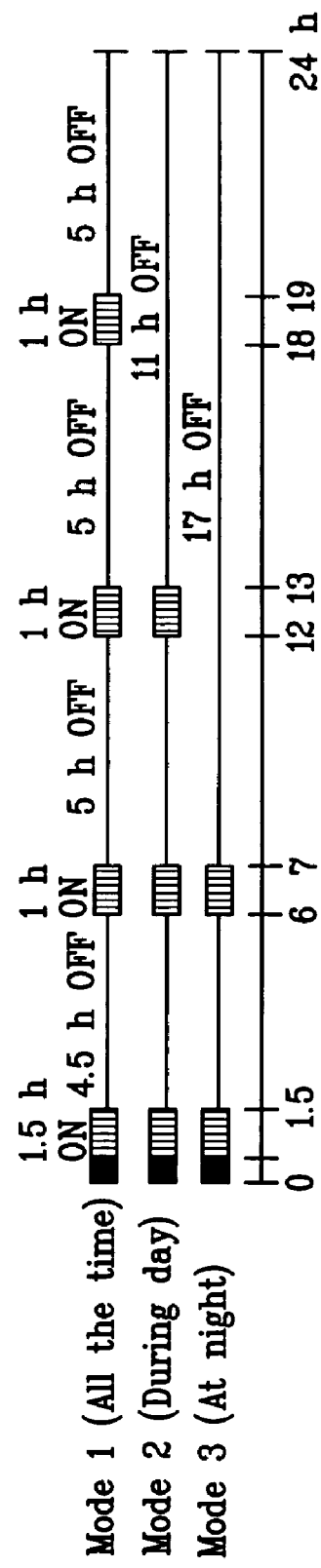

PORTABLE ELECTROTHERAPY DEVICE FOR TREATING OSTEOARTHRITIS AND OTHER DISEASES, DEFECTS AND INJURIES OF THE KNEE JOINT

CROSS-REFERENCE TO RELATED PATENT APPLICATIONS

The present application is a Continuation-in-Part of currently U.S. patent application Ser. No. 10/457,167 filed June 9, 2003 now U.S. Pat. No. 7,022,506, entitled "Method and Device for Treating Osteoarthritis, Cartilage Disease, Defects and Injuries in the Human Knee," which is a Continuation-in-Part of currently pending U.S. patent application Ser. No. 10/257,126, filed Oct. 8, 2002, entitled "Regulation of Genes Via Application of Specific and Selective Electrical and Electromagnetic Signals," which claims priority from International Application No. PCT/US01/05991 filed Feb. 23, 2001, which, in turn, claims priority to U.S. Provisional Application Ser. No. 60/184,491 filed Feb. 23, 2000. The present application is also related to U.S. patent application Ser. No. 10/255,241, filed Sep. 26, 2002, entitled "Regulation of Aggrecan Gene Expression with a Specific and Selective Electrical Signal," Ser. No. 10/267,708, filed Oct. 9, 2002, entitled "Regulation of Type II Collagen Gene Expression with a Specific and Selective Electrical Signal", and Ser. No. 10/461,188, filed June 13, 2003, entitled "Regulation of Matrix Metalloproteinase Gene Expression Using Specific and Selective Electrical and Electromagnetic Signals." The contents of these applications are hereby incorporated by reference.

FIELD OF THE INVENTION

The present invention is directed to a device and a method of designing a device that will deliver specific and selective electrical and electromagnetic signals to diseased articular cartilage for the treatment of osteoarthritis, cartilage disease, defects and injuries in the knee joint.

DESCRIPTION OF THE PRIOR ART

The present inventor has disclosed in the above-mentioned related applications methods and devices for specifically and selectively up-regulating gene expression of aggrecan (increase in aggrecan mRNA) and Type II collagen (increase in Type II collagen mRNA) and down-regulating gene expression of metalloproteases (decrease in MMP-I, MMP-3 and MMP-13) by applying specific and selective electrical and electromagnetic signals to the knee joint in patients afflicted with osteoarthritis, cartilage disease, defects and injuries. As described in these patent applications, specific and selective capacitively coupled electric fields of 10–20 mV/cm amplitude at a frequency of 60 kHz and a sine wave configuration showed achieved maximum up-regulation of aggrecan mRNA when the electric signal was applied for 1 hour at a 50% duty cycle, maximum up-regulation of Type II collagen mRNA when the electric signal was applied for 30 minutes at a 8.3% duty cycle, and maximum down-regulation of MMP-I when the electric signal was applied at a duty cycle of 100% for 30 minutes. It is desired to develop a device that is specifically designed to selectively generate such signals for up-regulating the expression of various genes (for example aggrecan mRNA, Type II collagen mRNA) with specific and selected signals and also-down-regulating the expression of other genes (for example, MMP-1, MMP-3, MMP-4) in the treatment of osteoarthritis, cartilage disease, defects and injuries of the knee. Preferably, the device is portable and can be programmed to deliver a wide variety of specific signals to regulate gene expression in a wide variety of selected diseases of the musculoskeletal system (bone, cartilage, tendon, and muscle), the cardiovascular system (angiogenesis, vascular repair, revascularization), skin and wound healing, and in preventing tumor metastases. The present invention is designed to meet these needs in the art.

SUMMARY OF THE INVENTION

The present invention meets the afore-mentioned needs in the art by providing a non-invasive electromagnetic therapeutic method and apparatus for treating diseased and injured tissue in a human knee joint. Such a method in accordance with the invention includes the step of generating compound electric signals comprising a 60 kHz sine wave having a peak to peak voltage of approximately 4.6 V to 7.6 V and a 100% duty cycle signal that is generated for approximately 30 minutes and a 50% duty cycle signal that is generated for approximately 1 hour after the 100% duty cycle signal. These signals selectively up-regulate Aggrecan and Type II Collagen gene expression while selectively down-regulating metalloproteases. These compound electric signals are communicated to electrodes or coils in the proximity of a patient's knee for the generation of a specific and selective electromagnetic field that treats the diseased and/or injured tissue.

In accordance with the method of the invention, different duty cycle modes may be selected for generation during a 24 hour time period. In a first mode, the compound electric signal and 3 additional 50% duty cycle signals are generated; in a second mode, the compound electric signal and 2 additional 50% duty cycle signals are generated; and in a third mode, the compound electric signal and 1 additional 50% duty cycle signal is generated. Different voltage modes are selected in accordance with a circumference of the patient's knee.

A device for generating specific and selective signals for application to electrodes for generating selective electric or electromagnetic fields for the treatment of diseased tissue in a human knee joint in accordance with the invention includes a signal generator that generates compound electric signals that selectively up-regulates Aggrecan gene expression and/or Type II Collagen gene expression and selectively down-regulates metalloprotease gene expression and other proteases in the treatment of cancer and in the prevention of metastases of cancer, and an electric lead or a wireless connection that communicates the compound electric signals to the electrodes or coils for field generation. The signal generator may include a switch that may be manually or automatically switched to switch the signal generator into different modes on different days. A microcontroller in the signal generator is responsive to time of day data to selectively generate the compound electric signals at predetermined treatment times.

BRIEF DESCRIPTION OF DRAWINGS

The present invention will be better understood with reference to the accompanying figures, of which:

FIG. 3 is a graphic representation of the response of Type II collagen mRNA gene expression when articular cartilage chondrocytes are exposed to a 20 mV/cm capacitively coupled field of three different signal types in the presence of IL-1B. As indicated, the expression of Type II collagen mRNA is optimal with one compound signal (30 minutes 100% duty cycle followed immediately by a 50% duty cycle for 1 hour) versus one simple signal (30 minutes of 100% duty cycle) or the same simple signal repeated once.

FIG. 8 is a graphic representation of examples of various device signal modes. As illustrated, each mode begins with a compound signal (30 minutes 100% duty cycle/1 hour 50% duty cycle).

DETAILED DESCRIPTION OF THE ILLUSTRATIVE EMBODIMENTS

The invention will be described in detail below with reference to FIGS. 1–11. Those skilled in the art will appreciate that the description given herein with respect to those figures is for exemplary purposes only and is not intended in any way to limit the scope of the invention. All questions regarding the scope of the invention may be resolved by referring to the appended claims.

Definitions:

As used herein, the phrase "signal" is used to refer to a variety of signals including mechanical signals, ultrasound signals, electromagnetic signals and electric signals output by a device.

As used herein, the term "field" refers to an electrical field within targeted tissue, whether it is a combined field or a pulsed electromagnetic field or generated by direct current, capacitive coupling or inductive coupling.

Description of Illustrated Embodiments:

The invention is a portable device that enables the application of capacitive or inductively coupled electric fields to a patient's knee for providing a desired therapeutic effect. The device provides a system coordinator with control of the stimulation signal to the subject receiving treatment. The system coordinator receives total control of the primary program download and subsequent upgrades to the programming for device modification and allows limited control ability to the installer of the device to set fitting and mode: A variety of power sources or a fixed power source may be used to power the device. Time, day and date information is used to set mode parameters for different treatments at different times of day or the week. Such information is also useful in the storage and retrieval of dated records for historical evaluation.

The device of the invention is designed to emit signals of various durations, amplitudes, frequencies, duty cycles, and waveforms in various modes. The characteristics of the signals are selected to selectively up-regulate and down-regulate gene expressions as described in detail in the afore-mentioned related applications. Such signals are configured as simple or compound. A simple signal is defined as one signal of a given duration, amplitude, frequency, and duty cycle. A compound signal is defined as two or more simple signals applied sequentially, with or without an off break in between each simple signal. The simple signal components of a compound signal may be identical to each other or may vary one from another in duration, amplitude, frequency and/or duty cycle.

Figure 1:
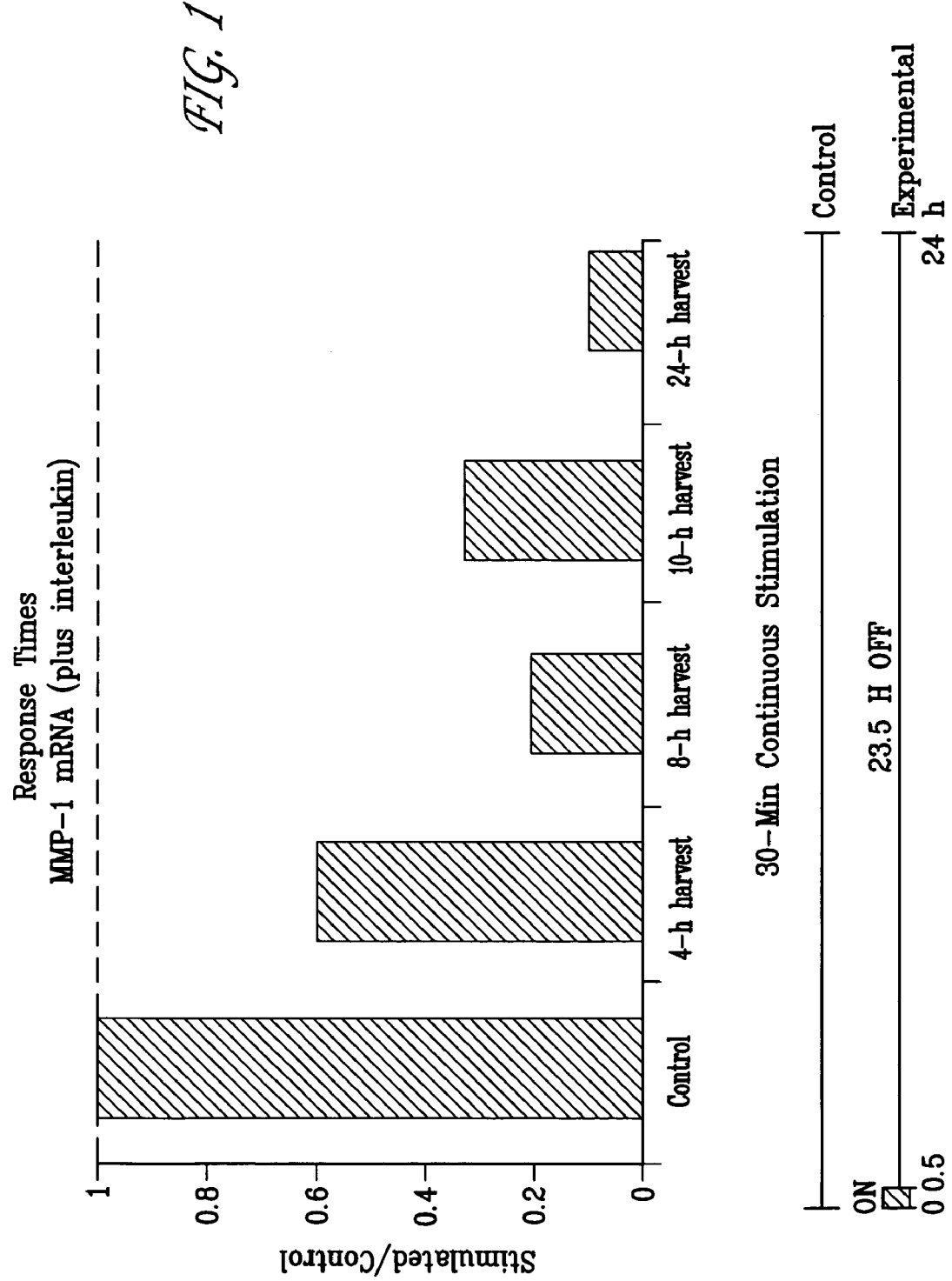
FIG. 1 is a graphic representation of the response of MMP-1 mRNA gene expression when articular cartilage chondocytes are exposed to a 20 mV/cm capacitively coupled field for 30 minutes of 100% duty cycle in the presence of interleukin (IL-1B). As indicated, the expression of MMP-1 mRNA decreased dramatically by the end of 24 hours.
Figure 2:
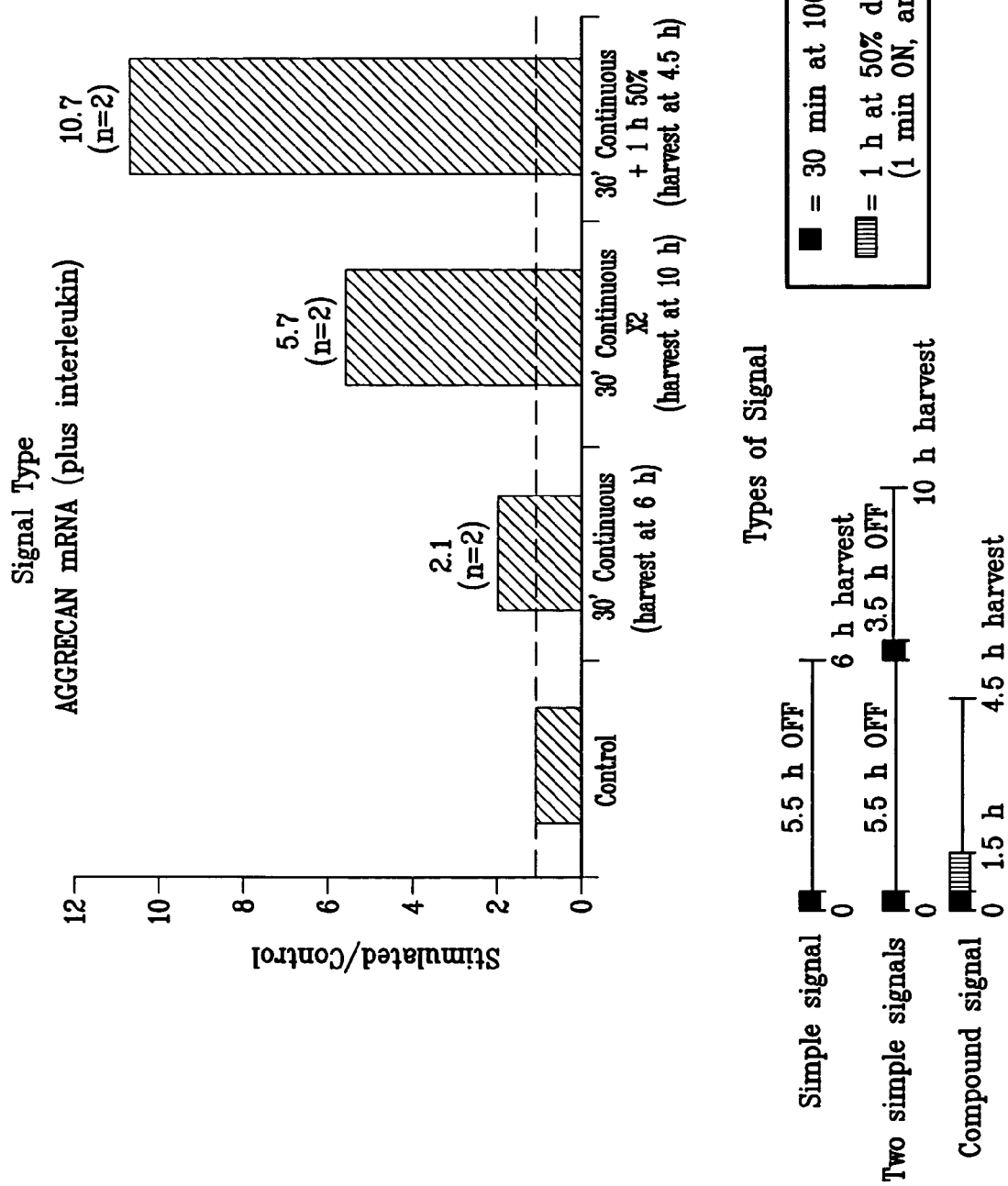
FIG. 2 is a graphic representation of the response of aggrecan mRNA gene expression when articular cartilage condrocytes are exposed to a 20 mV/cm capacitively coupled field of three different signal types in the presence of IL-1B. As indicated, the expression of aggrecan mRNA is optimal with one compound signal (30 minutes at 100% duty cycle followed immediately by a 50% duty cycle for 1 hour) versus one simple signal (30 minutes of 100% duty cycle) or the same simple signal repeated once.

Several examples of such signals are shown in the figures to illustrate how various signal constructs can be designed in order to achieve maximum regulation of selected gene expressions. For example, when articular cartilage chondrocytes grown in micromass are exposed to interleukin 1B (IL-1B), there is a dramatic increase in MMP-1 mRNA (as occurs in osteoarthritis). However, as shown in FIG. 1, when a capacitively coupled electric field of 20 mV/cm (sine wave, 60 kHz) with a 100% duty cycle is applied for 30 minutes, the down-regulation of MMP-1 mRNA is dramatic. Thus, only one 30 minute period of this specific signal per 24 hours is optimal for maintaining the down-regulation of MMP-1 mRNA and other proteases such as those used in the treatment of cancer and in the prevention of metastases in cancer. For up-regulation of aggrecan mRNA, however, a compound signal of 30 minutes of a 100% duty cycle followed immediately by a 50% duty cycle for 1 hour in the presence of IL-1B produces a 10-fold increase in aggrecan mRNA, as shown in FIG. 2. This compound signal is 5 fold more effective than are two simple signals, each of 30 minutes duration and 100% duty cycle, when the signals are applied 4 hours apart. As shown in FIG. 3, the up regulation of Type II collagen mRNA follows the same pattern since aggrecan and Type II collagen gene expressions are complimentary function-wise.

Figure 4:
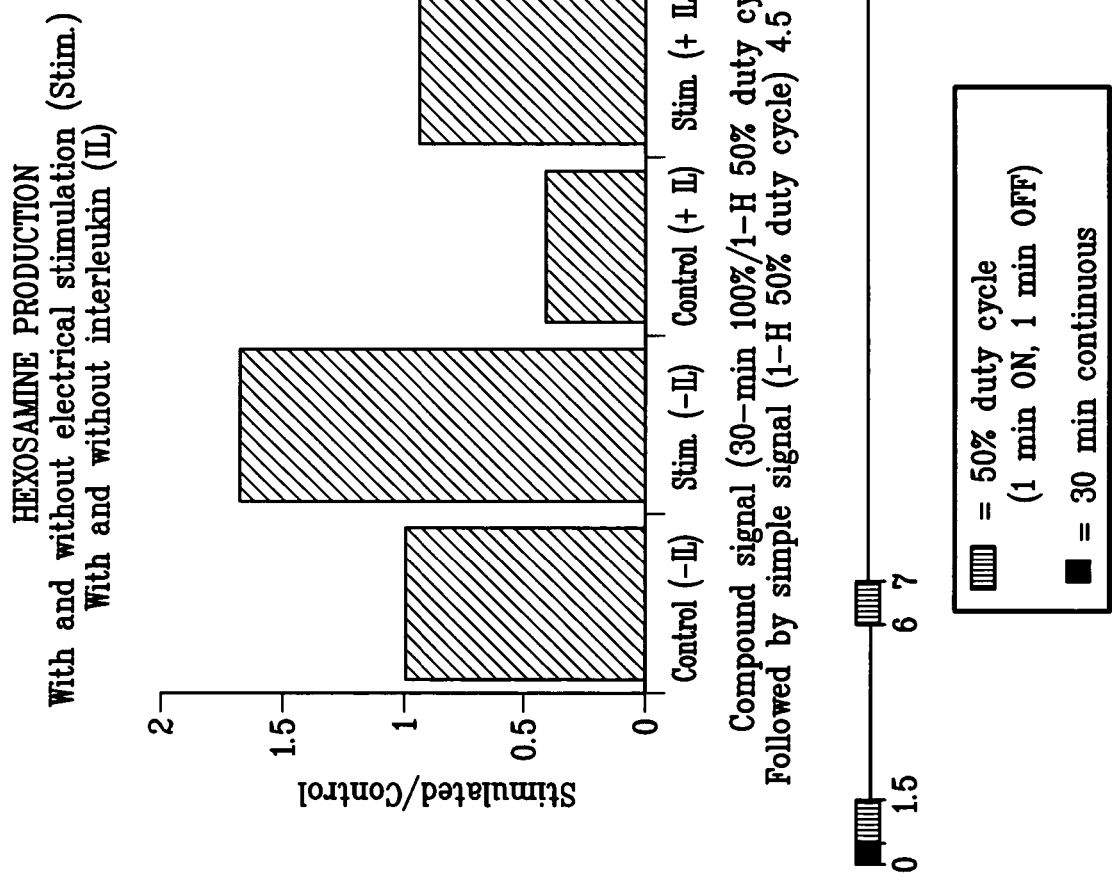
FIG. 4 is a graphic representation of hexosamine production when articular cartilage chondrocytes are exposed to a 20 mV/cm capacitively coupled field of a compound signal (30 minutes of 100% duty cycle for 30 minutes, followed immediately by a 50% duty cycle for 1) followed 4½ hours later by a simple signal of 50% duty cycle for 1 hour, with or without the presence of IL-1B in the media. As indicated, the electrical stimulation produced a 1.6 field increase in hexosamine in the absence of IL-1B and a 2.5 fold increase in hexosamine in the presence of IL-1B.
Figure 5:
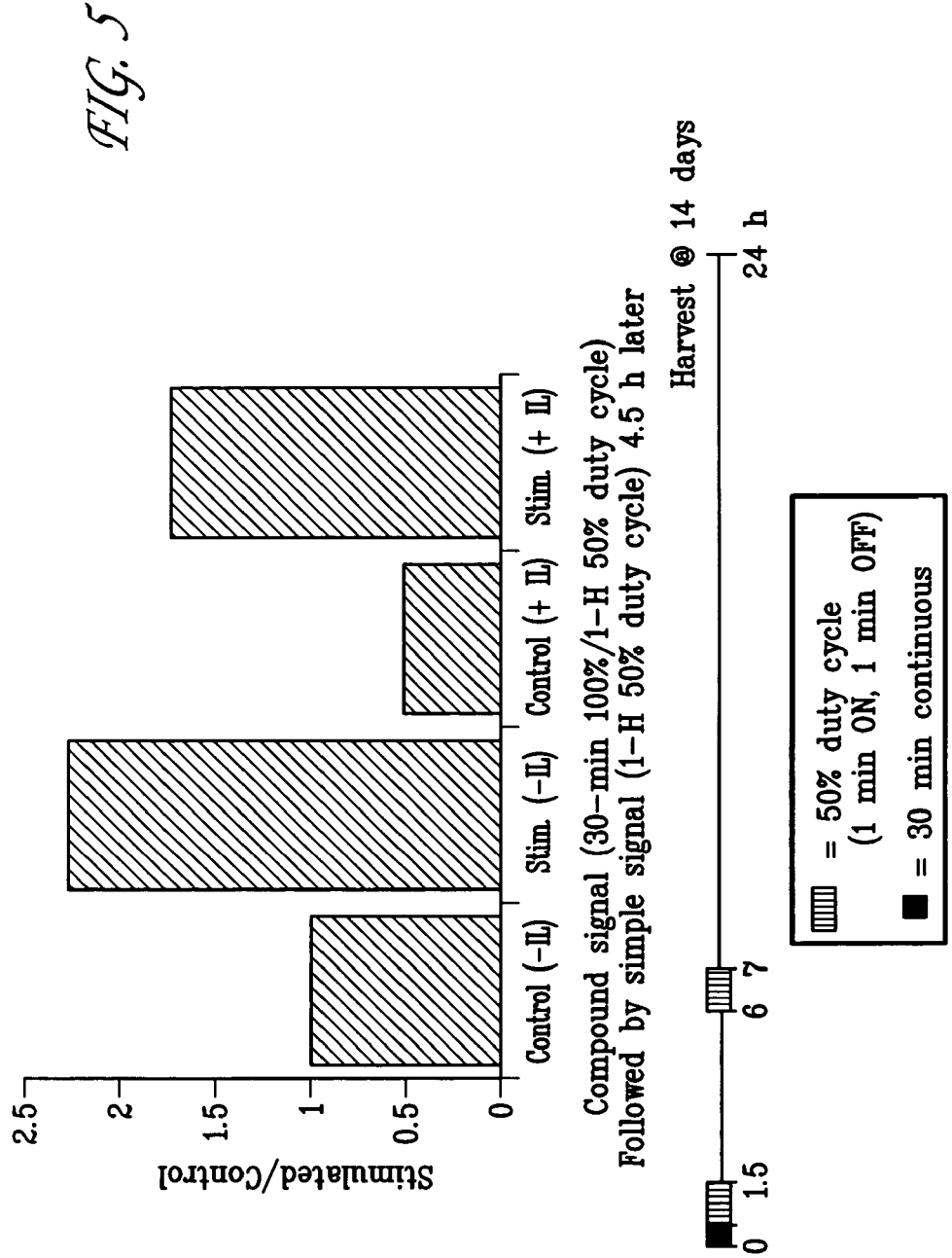
FIG. 5 is a graphic representation of hydroxyproline production when articular cartilage chondrocytes are exposed to a 20 mV/cm capacitively coupled field of a compound signal (30 minutes of 100% duty cycle followed immediately by a 50% duty cycle for 1 hour) followed 4½ hours later by a simple signal of 50% duty cycle for 1 hour, with and without the presence of IL-1B in the media. As indicated, the electrical stimulation produced a 1.7 fold increase in hydroxyproline in the absence of IL-1B and a 3-fold increase hydroxyproline in the presence of IL-1B.

The effects of various combinations of simple and compound signals in increasing the product of gene expressions, for example the increase in hexosamine production resulting from up-regulation of aggrecan mRNA and the increase in hydroxyproline production resulting from up-regulation of Type II collagen mRNA, are illustrated in FIGS. 4 and 5. Those skilled in the art will appreciate that the initial compound signal (consisting of 30 minutes of 100% duty cycle followed by 1 hour of 50% duty cycle) down regulates MMP-1 mRNA (initial 30 minutes) and up-regulates aggrecan mRNA and Type II collagen mRNA (next one hour). Another 50% duty cycle signal is applied 4.5 hours later to further boost gene expression for aggrecan mRNA and Type II collagen mRNA. It is not necessary to repeat the 30 minutes 100% duty cycle signal since the gene expression for MMP-1 is initially down regulated for a full 24 hours. (FIG. 1). As shown in FIGS. 4 and 5, the application of the signal constructs described above result in a 1.6 and 1.7 fold increase in the production of hexosamine and hydroxyproline, respectively, when IL-1B is absent, and an even larger increase when IL-1B is present (2.5 and 3 fold increase, respectively).

Figure 6:
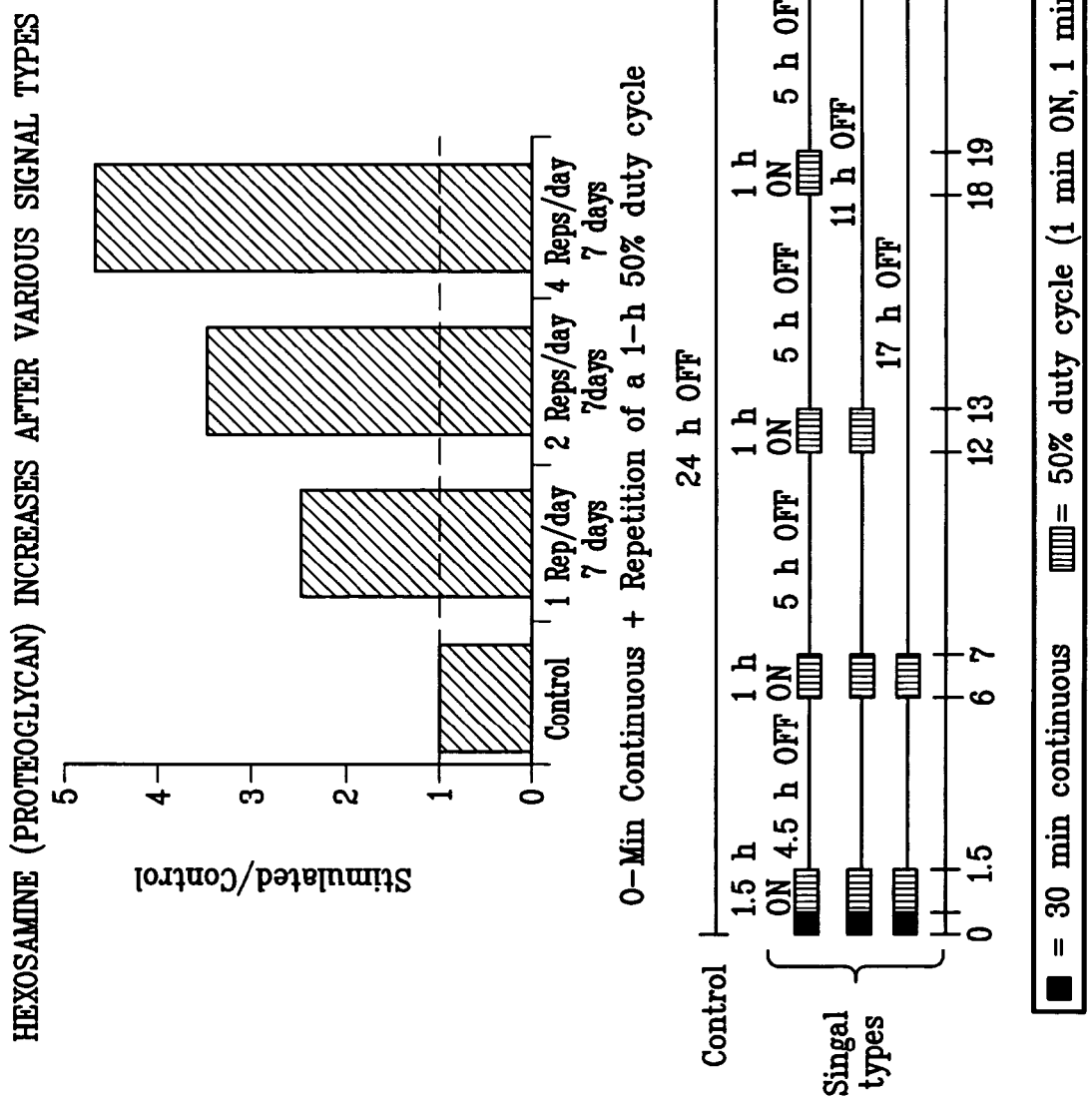
FIG. 6 is a graphic representation of hexosamine production when articular cartilage chondrocytes are exposed to a capacitively coupled field of various signal types. As indicated, a train of signals, consisting of a compound signal (30 minutes 100% duty cycle/1 hour 50% duty cycle) followed by 1 to 3 repetitions of a simple signal (each 1 hour of 50% duty cycle) gives almost a 5 fold increase in hexosamine production but lesser increases in hexosamine production with signal trains containing fewer repetitions of the simple signal (1 hour of 50% duty).
Figure 7:
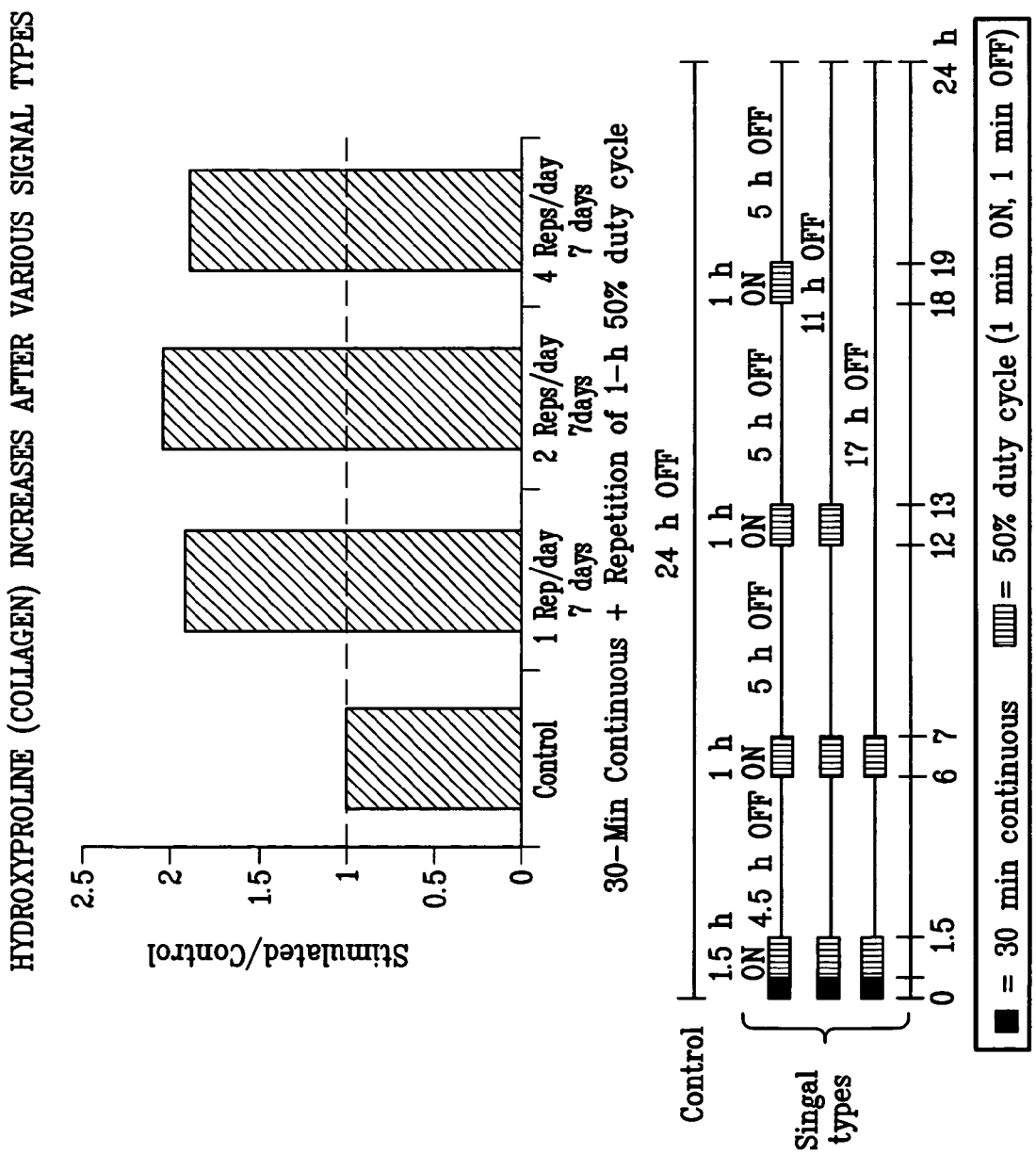
FIG. 7 is a graphic representation of hydroxyproline production when articular cartilage chondrocytes are exposed to a capacitively coupled field of various signal types. As indicated, a train of signals, consisting of a compound signal (30 minutes 100% duty cycle/1 hour 50% duty cycle) followed by 1 to 3 repetitions of simple signals (each 1 hour of 50% duty cycle) gives approximately a 2-fold increase in hydroxyproline production with one, two, or three repetitions of a simple signal.

For even greater increases in hexosamine production a third signal of 50% duty cycle boosts production 3.4 fold, and a fourth signal of 50% duty cycle boosts it to 4.8 fold per 24 hours (FIG. 6). Thus, a train of signals, the compound signal followed by three simple signals, provides maximum hexosamine production per 24 hours using this construct. As shown in FIG. 7, the same construct increases hydroxyproline production to 1.9, 2.0, and 1.9 fold, respectively. Other constructs can easily be devised by one knowledgeable in the field. For instance, an 8.3% duty cycle applied for 6 hours increases hyproxyproline by 5.1 fold. This could be configured with a 50% duty cycle applied for 1 hour for hexosamine stimulation along with a 100% duty cycle for a 30 minutes to down-regulate MMP-1. These examples are given to show how different gene expressions can be up-regulated and down-regulated in the same 24 hour signal construct.

The device of the invention is designed to provide one or more modes, each applying various signal constructs. For example, as shown in FIG. 8, one mode is designed to apply a compound signal followed by simple signals 4.5 hours, 5 hours, and again 5 hours apart during a 24 hour cycle. Mode 2 is designed to apply an initial compound signal followed by two simple signals 4.5 and 9.5 hours later during a 24 hour cycle. Mode 3 is designed to apply a compound signal and a simple signal 4.5 hours later during a 24 hour cycle. Thus, a patient may wear a device switched to Mode 1 for use 24 hours a day, or switched to Mode 2 for use during the daytime only, or switched to Mode 3 for use during the night only. It is obvious to anyone experienced in the field that the device can be configured to apply an electrical field of various wave forms, amplitudes, durations, frequencies, and duty cycles in various compound and simple signal construct in one or various modes on different days for various periods of time.

Figure 9A:
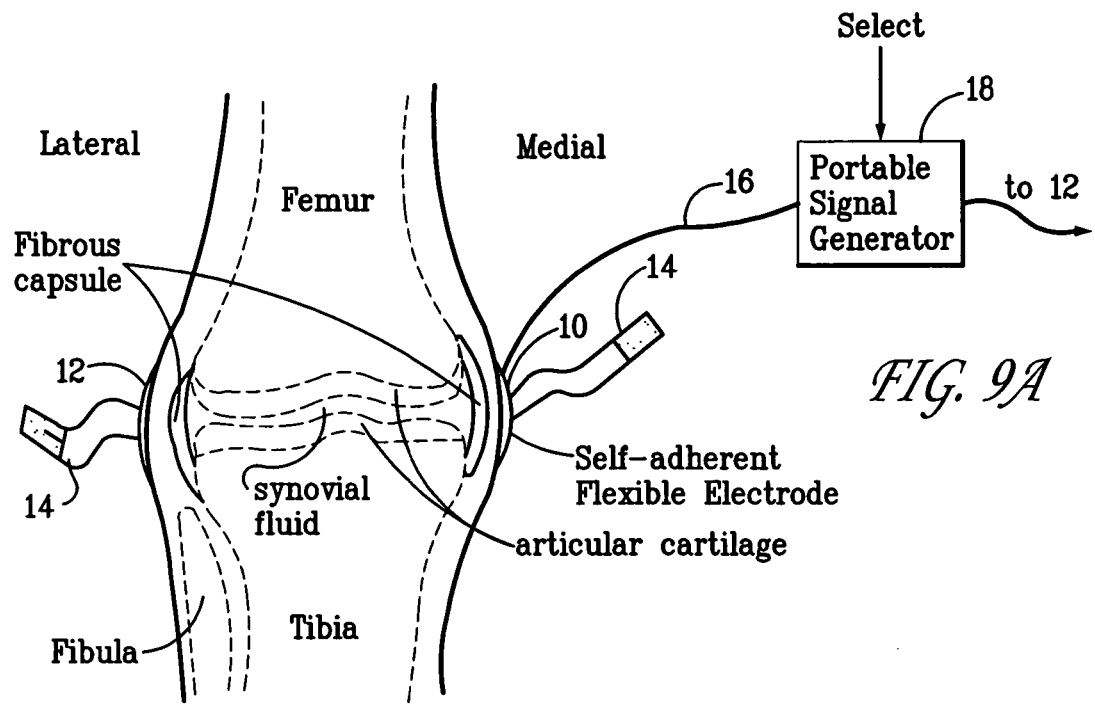
FIG. 9A is a pictorial representation of the human knee with self-adherent, flexible electrodes applied to the medial (inside) and lateral (outside) of the knee at the joint line for capacitive coupling.
Figure 9B:
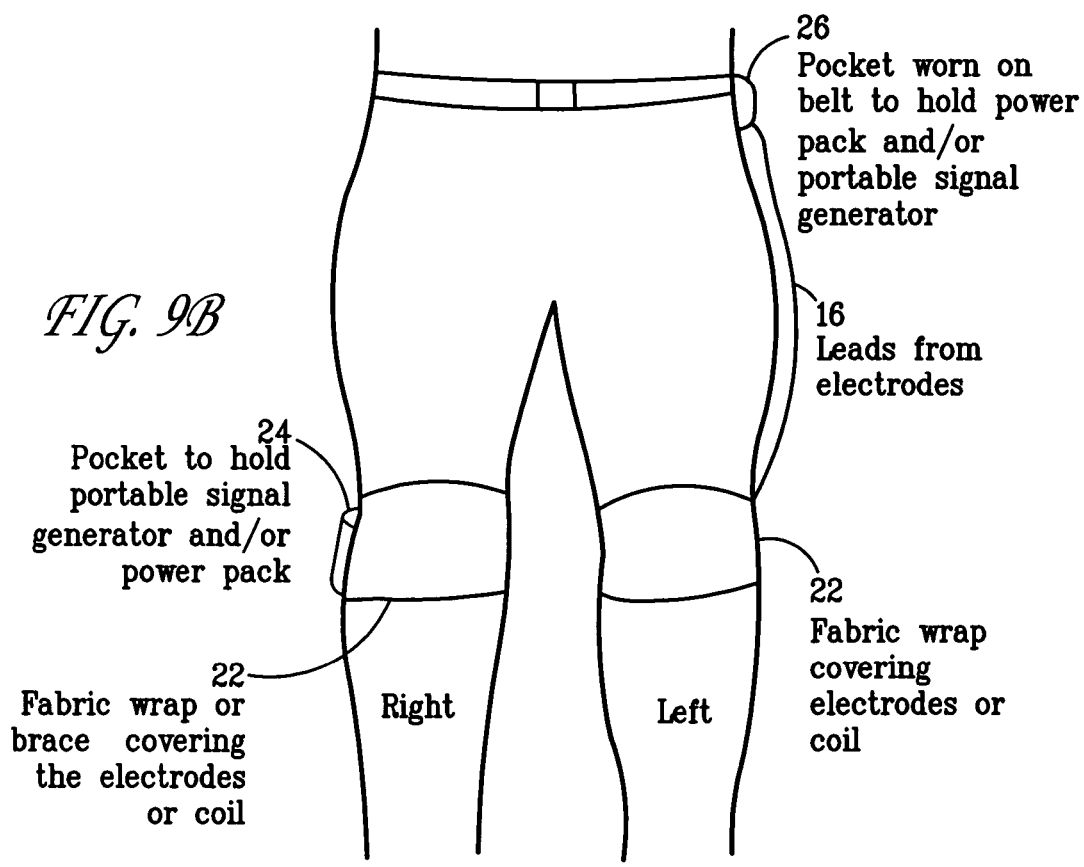
FIG. 9B is a pictorial representation of the lower torso with a fabric wrap or brace around the knees covering the electrodes or coils with a pocket in the wrap or brace (Right) to hold the portable signal generator and a pocket worn on the belt (Left) to hold the power pack.

As illustrated in FIG. 9A, the device of the invention may be connected to two flexible, self adherent, conductive electrodes 10, 12 placed on the skin on the medial (inside) and lateral (outside) of the knee at the joint line. A short VELCRO™ wrap 14 or other material may be wrapped around the electrodes 10, 12 to hold them in place, or the electrodes 10, 12 may be fitted into a fabric knee wrap or brace 22 as shown in FIG. 9B such that the electrodes 10, 12 are a replaceable part of the wrap or brace 22 and are held in the wrap or brace 22 in such a way as to ensure good contact at the desired location on the inside and outside of the knee at the level of the joint line.

The portable signal generator 18 of the invention is preferably small (approximately 3×2×½ inches), light-weight (6–8 oz), and powered by a standard battery (e.g., 9-volts). The device is portable and may be worn either attached to the knee wrap or brace 22 by a VELCRO™ strap 14 or fitted into a pouch 24 in the wrap or brace 22 with or without its battery pack, or the signal generator 18 may be worn at the belt line (waist) in pouch or holster 26 with or without (FIG. 9B) or above or below the knee by fitting into thigh or calf wraps secured by VELCRO™ straps or snaps (not shown). The portable signal generator is connected to each of the electrodes 10, 12 by one or more flexible leads 16, although a wireless connection (e.g., Bluetooth) may also be used.

The electrodes 10, 12 used in accordance with a capacitive coupling embodiment of the invention are flexible, non-metallic, approximately 2×2 inches each in size, and are self-adherent. One electrode is worn on the medial side of the knee and the other is worn on the lateral side of the knee as shown in FIG. 9A. As shown, both electrodes 10, 12 are placed at the approximate level of the knee joint. The electrodes 10, 12 are preferably disposable for replacement approximately every 5–7 days. The knee wrap or brace 22 either fits over the electrodes 10, 12 or the wrap or brace 22 contains a cut-out into which the electrodes 10, 12 can be placed for proper spacing on each side (medial and lateral) of the joint line.

Figure 9C:
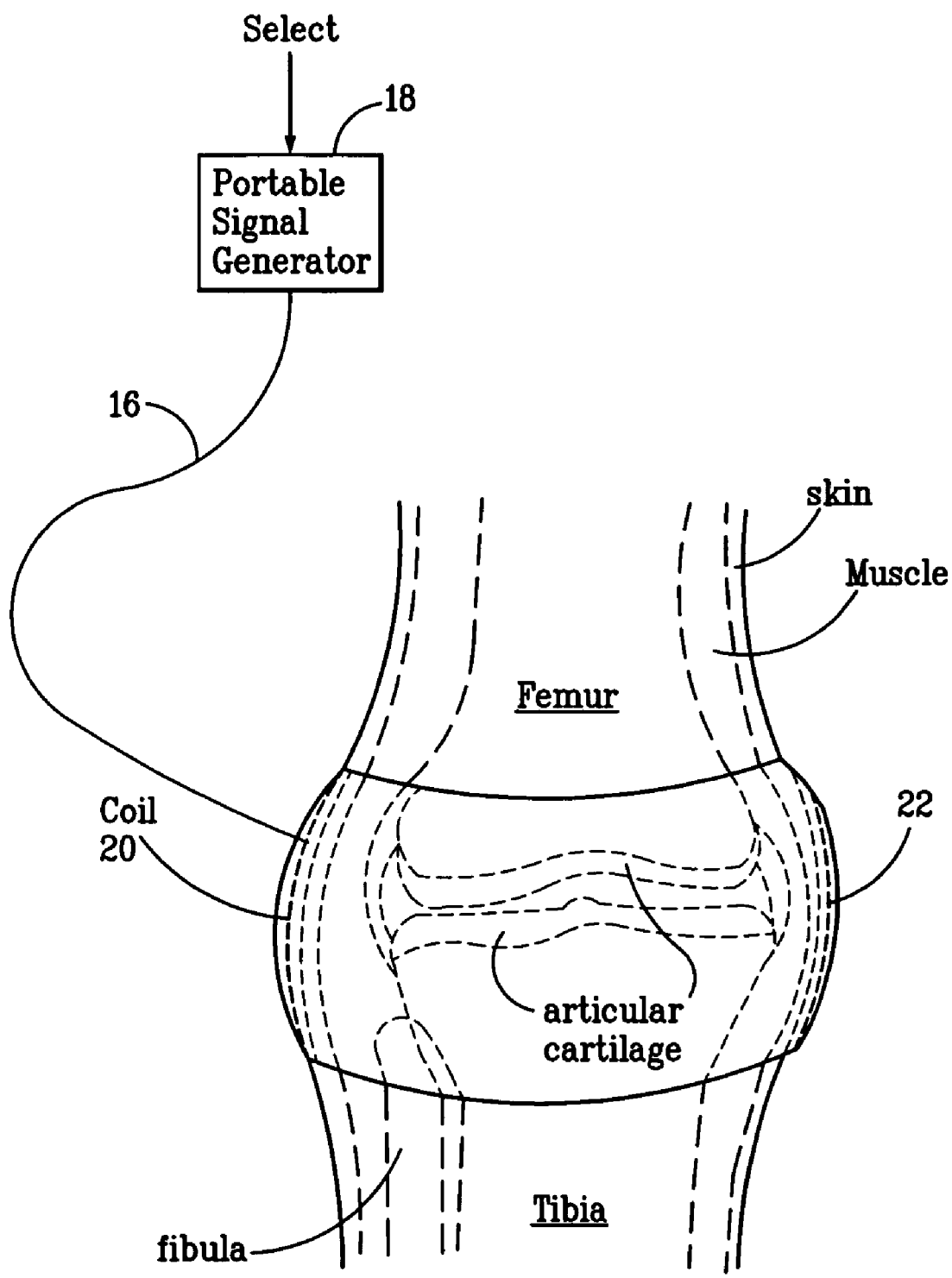
FIG. 9C is a pictorial representation of the human knee with a fabric wrap or brace around the knees covering a coil for inductive coupling.

In accordance with another implementation of the invention, the appropriate electric field can be delivered to diseased or traumatized articular cartilage using an inductive coupling device of the type shown in FIG. 9C. The electric field is generated in the knee by a coil 20 containing N turns that is inserted into a knee wrap or brace 22 and slipped over the knee and centered thereon. A battery-powered supply of current is attached to the coil leads from the portable signal generator such that a time varying current flows through the coil. This current produces a magnetic flux which in turn produces a time-varying electric field. It is understood that the current amplitude, frequency, duty cycle and wave form(s) can be controlled from the power supply so as to produce a therapeutic value for the E field.

As described in the aforementioned related application filed on Jun. 9, 2003, the voltage output by the portable signal generator 18 for application to the electrodes 10, 12 or the inductive coupling coil 20 is dependent upon the circumference of the patient's knee as follows:

| Switch Position | Knee Circumference | Voltage Output |
| --- | --- | --- |
| 1 | Small (less than 15 inches) | 4.6 V p-p ± 10% |
| 2 | Medium (15–16 inches) | 5.0 V p-p ± 10% |
| 3 | Large (16.1–18 inches) | 5.6 V p-p ± 10% |
| 4 | Extra Large (Greater than 18 inches) | 7.6 V p-p ± 10% |

In other words, different voltage outputs are provided at different switch positions of the device based on the size of the patient's knee joint. Current at the skin-electrode interface is set not to exceed 10 mAmps.

The Signal Mode is selected as follows:

| Signal Mode | Maximum Treatment Time |
| --- | --- |
| 1 | 24 hours/day |
| 2 | 16 hours/day |
| 3 | 8 hours/day |

Thus, a duty cycle/cycle time switch with 3 positions may be set in accordance with the signaling mode (8, 16, or 24 hours).

Preferably, the patient does not have access to the switches for setting voltage (based on knee size) and cycle time so that mode changes may be made only by the treating physician or nurse.

Figure 10:
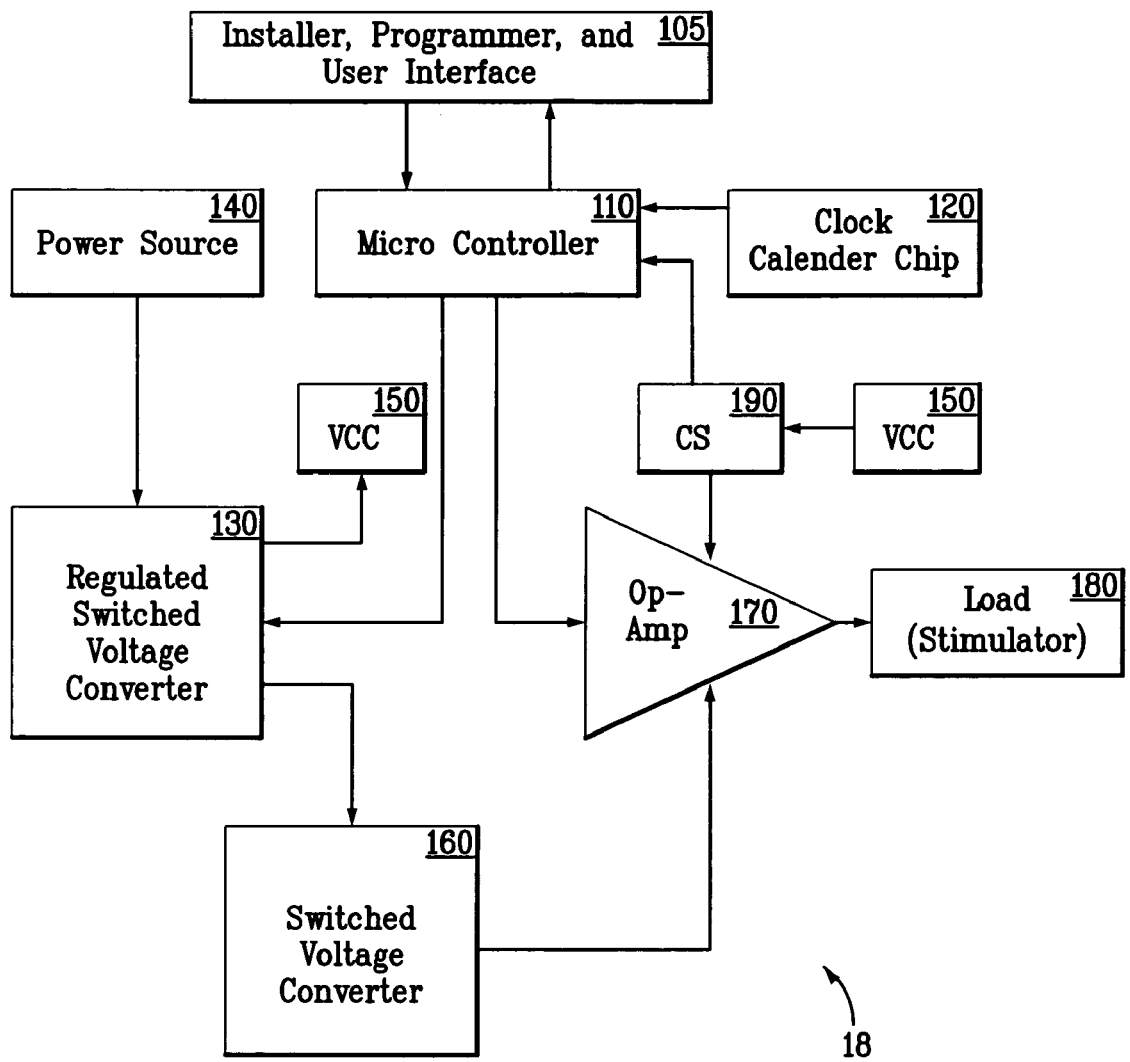
FIG. 10 is a block diagram of the circuitry of the portable signal generator device of the invention, where basic signal and control flows are indicated. Each block outlines specific circuits and their functions. VCC=Voltage Controlled Circuit or regulated voltage source, CS=Current Sense circuit, and Op-Amp=Operational Amplifier or Output drive amplifier.

Circuit Description:

FIG. 10 illustrates a circuit diagram of the portable electrotherapy device 18 of the invention. As illustrated, the patient (User) and Programmer's interface 105 is connected via a wired or wireless connection to a microcontroller 110 that downloads the operating system, source code, and application interface to display or retrieve information via a PC, laptop or PDA. The interface 105 also includes a power indicator (not shown) that lets the patient know that the device 18 is operational. The microcontroller 110 coordinates the user interface 105 with the rest of the circuit by executing stored program procedures. The device 18 operates as an independent controller that is not tethered to wires or display panels issuing control of the signal output according to date, day, and time of the operating program, as received from a clock calendar chip 120. The microcontroller 110 also retrieves data from the circuit such as current sense 190, power 140, 150 and day, date, and time from the clock calendar chip 120 and stores this data for later retrieval by the program coordinator (110, 105). The clock calendar chip 120 is preferably powered by a separate battery and maintains date, day, and time independently, thus allowing the microcontroller 110 an external reference that is unaffected by power or user interruption. The regulated switched voltage converter 130 accepts power from a variety of battery voltages or from a fixed power source 140 and supplies a regulated 5 volts (VCC) output 150 to power the device 18 and a switched 5 volt voltage output controlled by the microcontroller 110 to be supplied to the switched voltage converter 160. The switched voltage converter 160 takes a positive 5 volts in and creates a negative 5 volts output to supply to the output drive amplifier 170. The drive amplifier 170 under control of the microcontroller 110 supplies the output signal (4.6–7.6 volts peak-to-peak at less than 10 mAmps as determined by the installer) to the electrodes 10, 12 or the coil 20 via load stimulator 180.

The current is fed back in a feedback circuit (CS) 190, which senses the proper drain when the electrodes 10, 12 or coil 20 are positioned properly to let the program coordinator (or installer) know whether the device 18 and electrodes 10, 12 or coil 20 are properly attached to the patient for the period under evaluation. The load is the current draw that is encountered when the electrodes 10, 12 or coil 20 are properly placed and current flows so as to generate an electric field.

Figure 11:
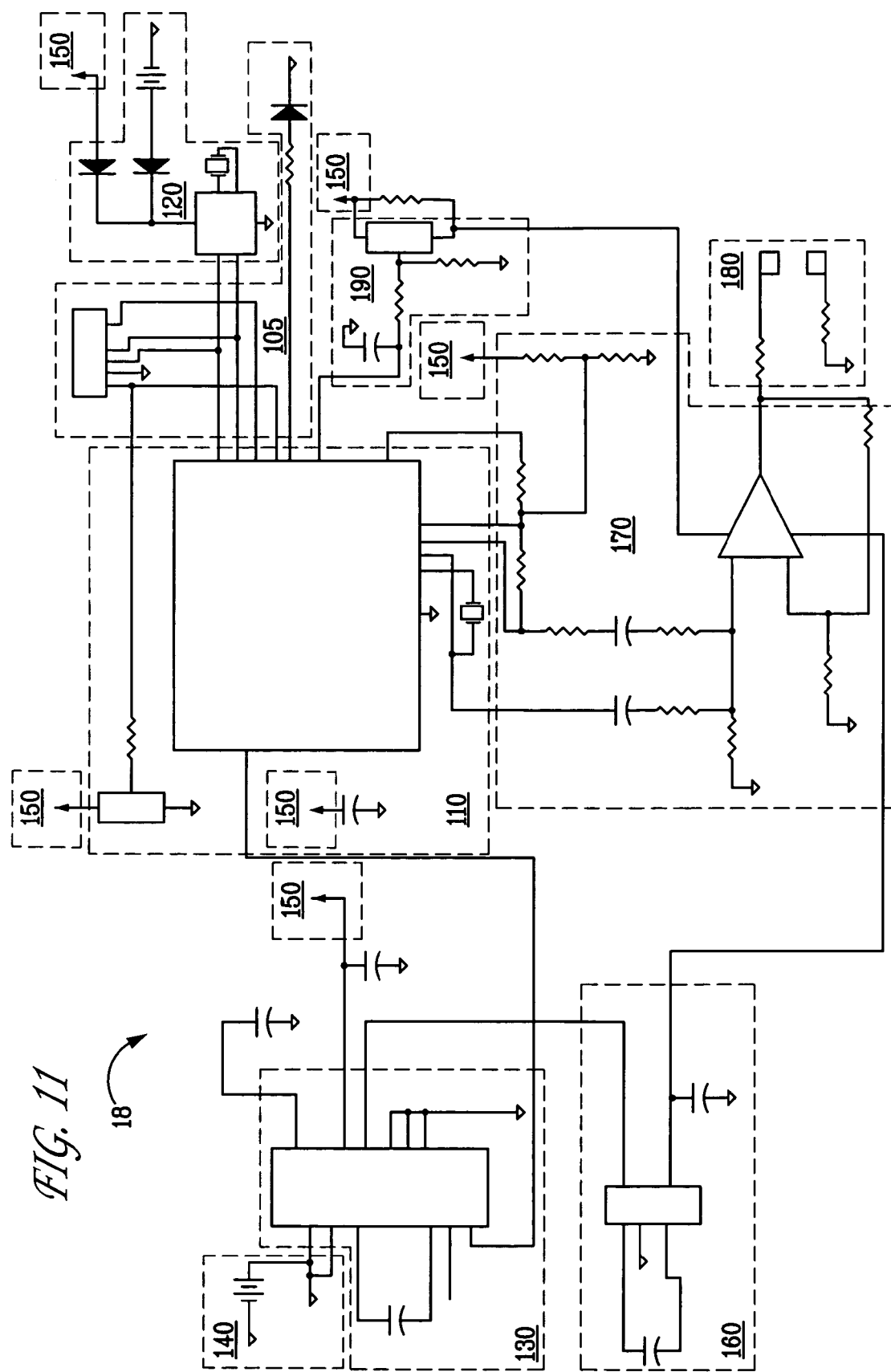
FIG. 11 is a schematic drawing of the circuit of FIG. 10.

The circuit schematic of the circuit of FIG. 10 is illustrated in FIG. 11. Like elements are illustrated by like reference numerals. Interface 105 of the device 18 includes the afore-mentioned switches for manually or automatically selecting the signal mode and the knee circumference. Preferably, these switches, whether manual or software implemented, may only be modified by the treating physician or nurse, thereby preventing the patient from modifying the treatment regimen. The actual mode and knee circumference switching is accomplished within the microcontroller 110. In one embodiment, the medical personnel or the patient may use a PC, PDA or other device to configure the device 18 via the interface 105 and microcontroller 110 as desired for proper operation. The patient will be able to determine that the power to the device 18 is ON if the power indicator LED of interface 105 is lit.

Those skilled in the art will appreciate that the device of the present invention may be used to provide drive signals to electrodes in a capacitive coupling embodiment and to coils or a solenoid in an inductive coupling embodiment. The same or an additional mode switch may be used to select between the capacitive and inductive coupling embodiments, with the respective drive signals provided accordingly.

Although implementations of the invention have been described in detail above, those skilled in the art will readily appreciate that many additional modifications are possible without materially departing from the novel teachings and advantages of the invention. Any such modifications are intended to be included within the scope of the invention as defined in the following claims.

We claim:

1. A device for generating specific and selective signals for application to a capacitive coupling and/or inductive coupling device for the generation of selective electric or electromagnetic fields in defective or diseased tissue in a human knee joint for the treatment of the defective or diseased tissue, comprising:

a signal generator that generates compound electric signals that selectively up-regulate at least one of Aggrecan gene expression and Type II Collagen gene expression and selectively down-regulates metalloprotease gene expression, said compound electric signals comprising respective signals each having a given duration, amplitude, frequency and duty cycle that is selective for regulating Aggrecan, Type II Collagen and/or metalloprotease gene expression; and means for communicating said compound electric signals to said capacitive and/or inductive coupling device.

2. A device as in claim 1, wherein said compound electric signals comprise a 60 kHz sine wave having a peak to peak voltage of approximately 4.6 V to 7.6 V.

3. A device as in claim 2, wherein said compound electric signals comprise a 100% duty cycle signal that is generated for approximately 30 minutes and a 50% duty cycle signal that is generated for approximately 1 hour after said 100% duty cycle signal.

4. A device as in claim 3, wherein said signal generator further generates during a 24 hour time period at least one additional 50% duty cycle signal having a duration of approximately 1 hour.

5. A device as in claim 4, wherein said signal generator is selectable into at least three modes, a first mode for generating during a 24 hour time period said compound electric signal and three of said additional 50% duty cycle signals, a second mode for generating during a 24 hour time period said compound electric signal and two of said additional 50% duty cycle signals, and a third mode for generating during a 24 hour time period said compound electric signal and one of said additional 50% duty cycle signals.

6. A device as in claim 5, wherein said signal generator comprises a switch that may be manually or automatically switched to switch said signal generator into different modes.

7. A device as in claim 1, further comprising means for holding said signal generator in proximity of a patient for communication with said capacitive and/or inductive coupling device.

8. A device as in claim 7, wherein said holding means comprises a Velcro™ strap that holds said signal generator to one of a patient's leg and a knee wrap.

9. A device as in claim 7, wherein said holding means comprises a pocket in one of a knee wrap and leg wrap.

10. A device as in claim 7, wherein said holding means comprises one of a pocket and a holster worn at the patient's waist.

11. A device as in claim 1, wherein said communicating means comprises one of an electric lead and a wireless connection.

12. A device as in claim 1, wherein said signal generator comprises a microcontroller responsive to time of day data to selectively generate said compound electric signals at predetermined treatment times.

13. A device as in claim 1, wherein said signal generator is selectable to generate said compound electric signal at different voltages in accordance with a circumference of a patient's knee.

14. A device for generating specific and selective signals for application to a capacitive coupling and/or inductive coupling device for the generation of selective electric or electromagnetic fields in defective or diseased tissue for the treatment of cancer and in the prevention of metastases in cancer in the defective or diseased tissue, comprising:

a signal generator that generates compound electric signals that selectively up-regulate at least one of Aggrecan gene expression and Type II Collagen gene expression and selectively down-regulates the gene expression of metalloproteases and other proteases in the treatment of cancer and in the prevention of metastases in cancer, said compound electric signals comprising respective signals each having a given duration, amplitude, frequency and duty cycle that is selective for regulating Aggrecan, Type II Collagen, metalloprotease and/or protease gene expression; and means for communicating said compound electric signals to said capacitive and/or inductive coupling device.

* * * * *

UNITED STATES PATENT AND TRADEMARK OFFICE
CERTIFICATE OF CORRECTION

| | |
|---|---|
| PATENT NO. | : 7,130,692 B2 |
| APPLICATION NO. | : 10/603226 |
| DATED | : October 31, 2006 |
| INVENTOR(S) | : Carl T. Brighton et al. |

Page 1 of 1

It is certified that error appears in the above-identified patent and that said Letters Patent is hereby corrected as shown below:

Title Page,
Item (56), page 2, col. 2, line 16, References Cited, OTHER PUBLICATIONS: "Lorich, D.G., et al." reference, delete "resopnse" and insert -- response --.

Signed and Sealed this

Tenth Day of April, 2007

JON W. DUDAS
*Director of the United States Patent and Trademark Office*